(12) United States Patent
Armstrong et al.

(10) Patent No.: US 12,087,418 B1
(45) Date of Patent: Sep. 10, 2024

(54) SYSTEMS AND METHODS FOR FACILITATING ORDER AND DELIVERY OF PRESCRIPTION MEDICATION

(71) Applicant: WALGREEN CO., Deerfield, IL (US)

(72) Inventors: Kevin MacKenzie Armstrong, Chicago, IL (US); Nicholas Phillip Baldwin, Chicago, IL (US)

(73) Assignee: WALGREEN CO., Deerfield, IL (US)

( * ) Notice: Subject to any disclaimer, the term of this patent is extended or adjusted under 35 U.S.C. 154(b) by 748 days.

(21) Appl. No.: 17/079,387

(22) Filed: Oct. 23, 2020

(51) Int. Cl.
G06Q 10/00 (2023.01)
G06Q 10/0836 (2023.01)
G06Q 10/087 (2023.01)
G06Q 10/1093 (2023.01)
G06Q 50/40 (2024.01)
G16H 20/10 (2018.01)

(52) U.S. Cl.
CPC ......... G16H 20/10 (2018.01); G06Q 10/0836 (2013.01); G06Q 10/087 (2013.01); G06Q 10/1093 (2013.01); G06Q 50/40 (2024.01)

(58) Field of Classification Search
None
See application file for complete search history.

(56) References Cited

U.S. PATENT DOCUMENTS

2014/0379371 A1* 12/2014 Tran ........................ G16H 20/10 705/2
2015/0242592 A1* 8/2015 Weiss ...................... G16H 10/60 705/2
2016/0063604 A1* 3/2016 Shaffer .............. G06Q 30/0261 705/26.81
2017/0091395 A1* 3/2017 May ........................ G16H 20/10
2019/0005449 A1* 1/2019 Smith ................ G06Q 10/0838

OTHER PUBLICATIONS

Sam's Club Pickup Receipt, May 1, 2020, Sam's Club (Year: 2020).*
Drug plan coverage rules, Apr. 15, 2020, Medicare.gov (Year: 2020).*
Martin Beck, Can you predict if a customer will make a purchase on a website?, Dec. 16, 2019 (Year: 2019).*
Store Pickup, Oct. 30, 2021, Walgreen, printed through www.archive.org (Year: 2021).*

* cited by examiner

Primary Examiner — Naresh Vig
(74) Attorney, Agent, or Firm — MARSHALL, GERSTEIN & BORUN LLP; Randall G. Rueth

(57) ABSTRACT

The following relates generally to facilitating order and delivery of prescription medication. In some embodiments, a first prescription for a first medication of a first patient is received; and a second prescription for a second medication of a second patient is received. A pickup time of a first pharmacy may then be determined by: determining a pickup time for the first medication at the first pharmacy; determining a pickup time for the second medication at the first pharmacy; and selecting, as the pickup time of the first pharmacy, the later of the pickup time for the first medication and the pickup time for the second medication. Identifications of all of: the first patient, the second patient, the first medication, the second medication, the first pharmacy, and the pickup time of the first pharmacy may then be displayed.

19 Claims, 21 Drawing Sheets

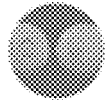
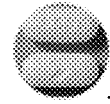
FIG. 2

Prescriptions (2)

Alex — 2 prescriptions ^

210A — Metformin
30mg tablets
Quantity — 30
Last filled price — $9.00

210B — Amoxicilin
30mg tablets
Quantity — 30
Last filled price — $9.00

Need to make a change? You can edit your order before you submit it.

410 — Add more prescriptions

710 — Remove prescriptions

720 → Fulfillment options

730 — Pick up in-store       740 — Deliver to you for $4.99

Ready for pickup today after 6pm
430 — 122 S. Michigan Ave.
0.1 mi • Chicago
• Pharmacy open until 9pm
• Store and Photo open until 10pm ( Change pickup location )

750 — Save time & prepay
Get through checkout quicker by paying before you pick up.

630 — Visa *7129   Expires 12/22 >

470 — Estimated total
480 — Prescription total — $18.00
Estimated tax — $0.90
Estimated total — $18.90 — 490

Submit Order

Charge will appear as a pending transaction until prescription has been picked up.

< Choose Delivery Address

1010 — Use saved address
251 Randolph Ave. >
Forest Park, IL 60594

1020 — New address >
Enter a new address for this order

FIG. 10

SYSTEMS AND METHODS FOR FACILITATING ORDER AND DELIVERY OF PRESCRIPTION MEDICATION

BACKGROUND

In the modern age, an efficient, streamlined process for order and delivery of prescription medication is essential. However, many current systems for order and delivery of prescription medication are cumbersome or inefficient.

The systems and methods disclosed herein provide solutions to these problems and others.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one aspect, there is a computer-implemented method for facilitating order and delivery of prescription medication. The method may include: receiving a first prescription for a first medication of a first patient; receiving a second prescription for a second medication of a second patient; and determining a pickup time of a first pharmacy. The determining of the pickup time of the first pharmacy may occur by: determining a pickup time for the first medication at the first pharmacy; determining a pickup time for the second medication at the first pharmacy; and selecting, as the pickup time of the first pharmacy, the later of the pickup time for the first medication and the pickup time for the second medication. The method may further include: displaying, on a display, identifications of all of: the first patient, the second patient, the first medication, the second medication, the first pharmacy, and the pickup time of the first pharmacy.

BRIEF DESCRIPTION OF THE DRAWINGS

FIG. 2 shows an example embodiment including access to information from multiple family members.

FIG. 7 illustrates an example including fulfillment options.

FIG. 10 illustrates an example of a screen for selecting whether a saved address will be used, or a new address will be entered.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

DETAILED DESCRIPTION

The present embodiments relate to order and delivery of prescription medication. In this regard, one objective of the present application is to provide more convenient and efficient access to prescription medication.

Exemplary Infrastructure

Figure 1:
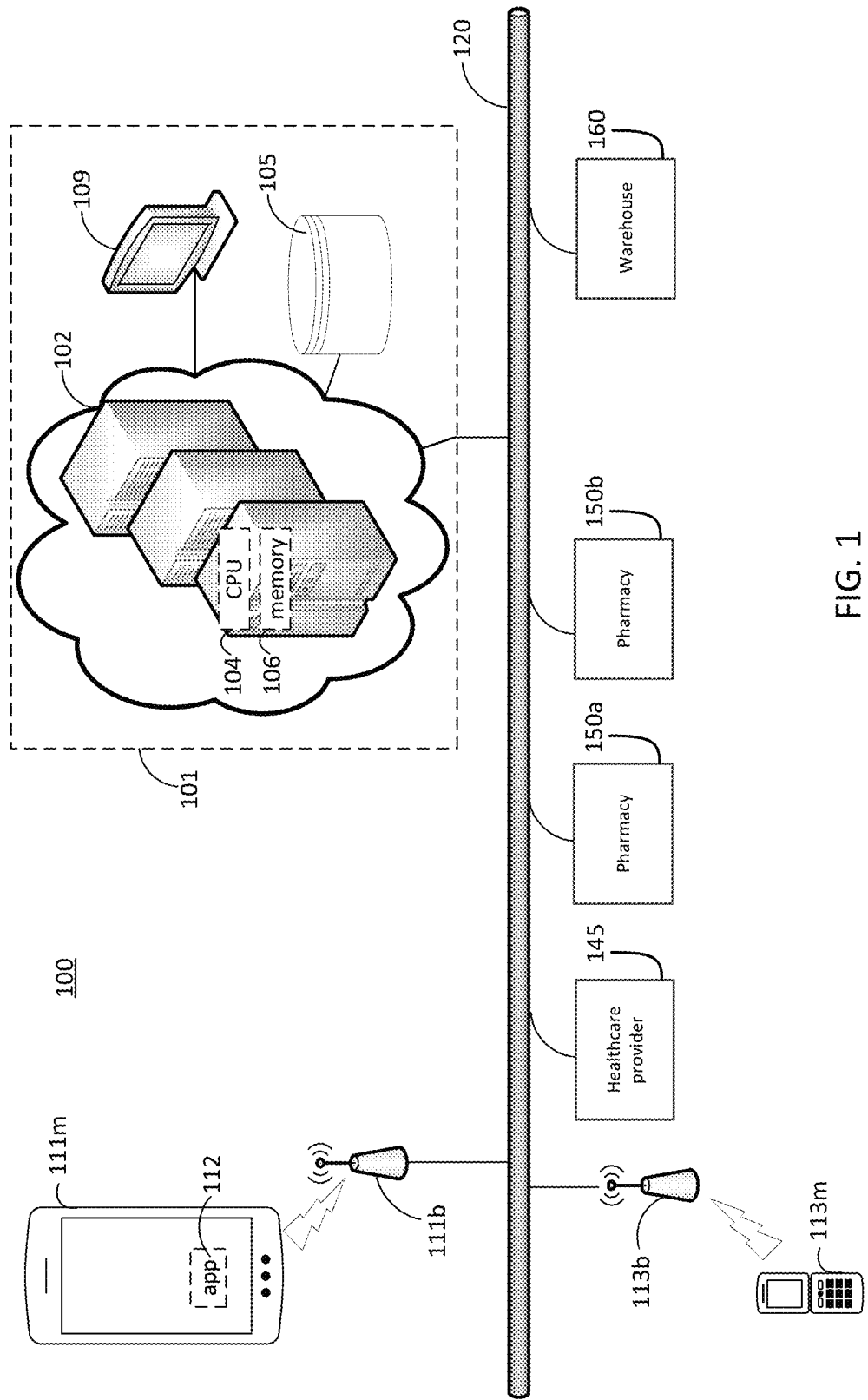
FIG. 1 illustrates a platform configured for facilitating order and delivery of prescription medication.

FIG. 1 illustrates a platform 100 configured for facilitating order and delivery of prescription medication in accordance with various embodiments disclosed herein. In the example embodiment of FIG. 1, the platform 100 includes prescription order and delivery system 101. In the example of FIG. 1, prescription order and delivery system 101 includes server(s) 102, which may comprise one or more computer servers. In various embodiments, server(s) 102 comprise multiple servers, which may comprise multiple, redundant, or replicated servers as part of a server farm. In still further embodiments, server(s) 102 are implemented as cloud-based servers. For example, server(s) 102 may comprise a cloud-based platform such as MICROSOFT AZURE, AMAZON AWS, or the like.

Server(s) 102 may include one or more processor(s) 104 as well as one or more computer memories 106. The memories 106 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memories 106 may store an operating system (OS) (e.g., Microsoft Windows, Linux, Unix, etc.) capable of facilitating the functionalities, apps, methods, or other software as discussed herein. The memories 106 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, the machine learning component and/or the provisioning application, where each are configured to facilitate their various functionalities discussed herein. It should be appreciated that one or more other applications may be envisioned and that are executed by the processor(s) 104.

The processor(s) 104 may be connected to the memories 106 via a computer bus responsible for transmitting electronic data, data packets, or otherwise electronic signals to and from the processor(s) 104 and memories 106 in order to implement or perform the machine readable instructions, methods, processes, elements or limitations, as illustrated, depicted, or described for the various flowcharts, illustrations, diagrams, figures, and/or other disclosure herein.

The processor(s) 104 may interface with the memory 106 via the computer bus to execute the operating system (OS). The processor(s) 104 may also interface with the memory 106 via the computer bus to create, read, update, delete, or otherwise access or interact with the data stored in the memories 106 and/or the database 105 (e.g., a relational database, such as Oracle, DB2, MySQL, or a NoSQL based database, such as MongoDB). The data stored in the memories 106 and/or the database 105 may include all or part of any of the data or information described herein, including, for example, the one or more search requests, the one or more transaction details, and the profile information of the user (e.g., patient or customer of a pharmacy).

The server(s) 102 may further include a communication component configured to communicate (e.g., send and receive) data via one or more external/network port(s) to one or more networks or local terminals, such as computer network 120 and/or terminal 109 (for rendering or visualizing) as described herein. In some embodiments, server(s) 102 may include a client-server platform technology such as ASP.NET, Java J2EE, Ruby on Rails, Node.js, a web service or online API, responsive for receiving and responding to electronic requests. The server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein. According to some embodiments, the server(s) 102 may include, or interact with, one or more transceivers (e.g., WWAN, WLAN, and/or WPAN transceivers) functioning in accordance with IEEE standards, 3GPP standards, 4G standards, 5G standards or other standards, and that may be used in receipt and transmission of data via external/network ports connected to computer network 120.

Server(s) 102 may further include or implement an operator interface configured to present information to an administrator or operator and/or receive inputs from the administrator or operator. As shown in FIG. 1, an operator interface may provide a display screen (e.g., via terminal 109). Server(s) 102 may also provide I/O components (e.g., ports, capacitive or resistive touch sensitive input panels, keys, buttons, lights, LEDs), which may be directly accessible via or attached to server(s) 102 or may be indirectly accessible via or attached to terminal 109. According to some embodiments, an administrator or operator may access the server(s) 102 via terminal 109 to review information, make changes, input training data, and/or perform other functions.

As described above herein, in some embodiments, server(s) 102 may perform the functionalities as discussed herein as part of a "cloud" network or may otherwise communicate with other hardware or software components within the cloud to send, retrieve, or otherwise analyze data or information described herein. Furthermore, server(s) 102 and/or their respective memorie(s) 106 are configured to store data including for example, patient data, pharmacy data, prescription data, and so forth.

In general, a computer program or computer based product, or application, in accordance with some embodiments may include a computer usable storage medium, or tangible, non-transitory computer-readable medium (e.g., standard random access memory (RAM), an optical disc, a universal serial bus (USB) drive, or the like) having computer-readable program code or computer instructions embodied therein, wherein the computer-readable program code or computer instructions may be installed on or otherwise adapted to be executed by the processor(s) 104 (e.g., working in connection with the respective operating system in memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C #, Objective-C, Java, Scala, Actionscript, Javascript, HTML, CSS, XML, etc.).

In the example embodiment of FIG. 1, the prescription order and delivery system 101, healthcare provider 145, pharmacies 150a, 150b, and warehouse 160 are communicatively connected, via computer network 120 and base stations 111b and 113b, to respective mobile devices 111m and 113m. Computer network 120 may comprise a packet based network operable to transmit computer data packets among the various devices and servers described herein. For example, computer network 120 may consist of any one or more of Ethernet based network, a private network, a local area network (LAN), and/or a wide area network (WAN), such as the Internet. In addition, in some embodiments, computer network 120 may comprise cellular or mobile networks to facilitate data packet traffic (e.g., mobile device movement data) to and from base stations 111b and/or 113b. Base stations 111b and 113b may comprise cellular towers or access points implementing any one or more cellular or mobile device standards, including, for example, any of GSM, UMTS, CDMA, NMT, LTE, 5G NR, or the like.

Exemplary Embodiments

The example platform 100 may be leveraged to improve order and delivery of prescription medication. For instance, app 112 may advantageously allow access to information of prescription medication for multiple family members. In this regard, the example of FIG. 2, shows a screenshot displayed by app 12 including the names of family members 201a, 201b, 201c. The example of FIG. 2 further illustrates first prescription 210A and second prescription 210B, which correspond to patient 201A. A user may toggle between family members 201A, 201B, 201C by clicking on the name of the family member. Furthermore, by clicking "view all," the user may view all family members.

FIG. 2 further illustrates status bar 220, which indicates a status of an order (e.g., in progress, delayed, filled, etc.). In this regard, it may be noted that, in the example of FIG. 2, the prescriptions Metformin, and Lipitor comprise a single order.

Figure 3:
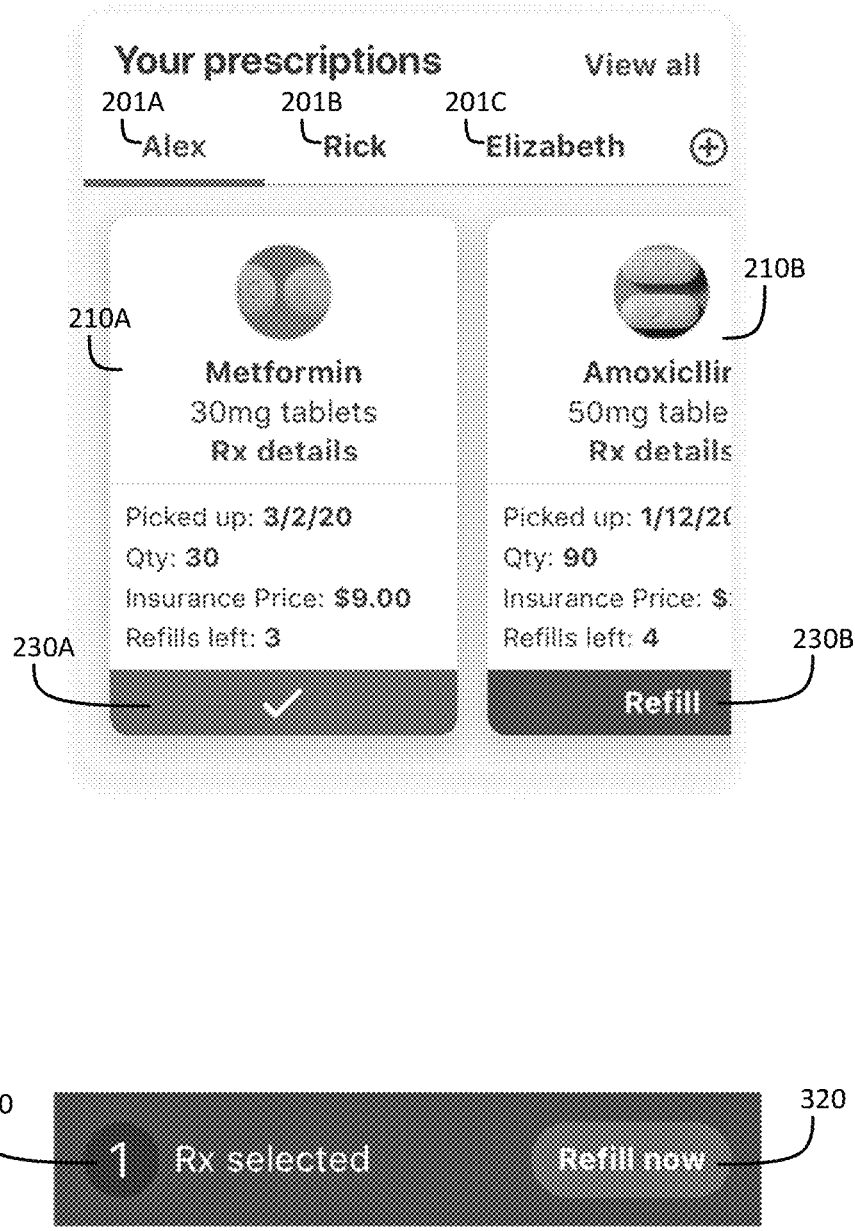
FIG. 3 shows an example implementation of a user selecting a refill button.

Furthermore, a user may refill a medication by pressing a refill button 230A or 230B. In some implementations, if a user presses button 230A in FIG. 2, the screen of FIG. 3 will be displayed, which shows a quantity of Rx selected indication 310, and refill now button 320.

Figure 4:
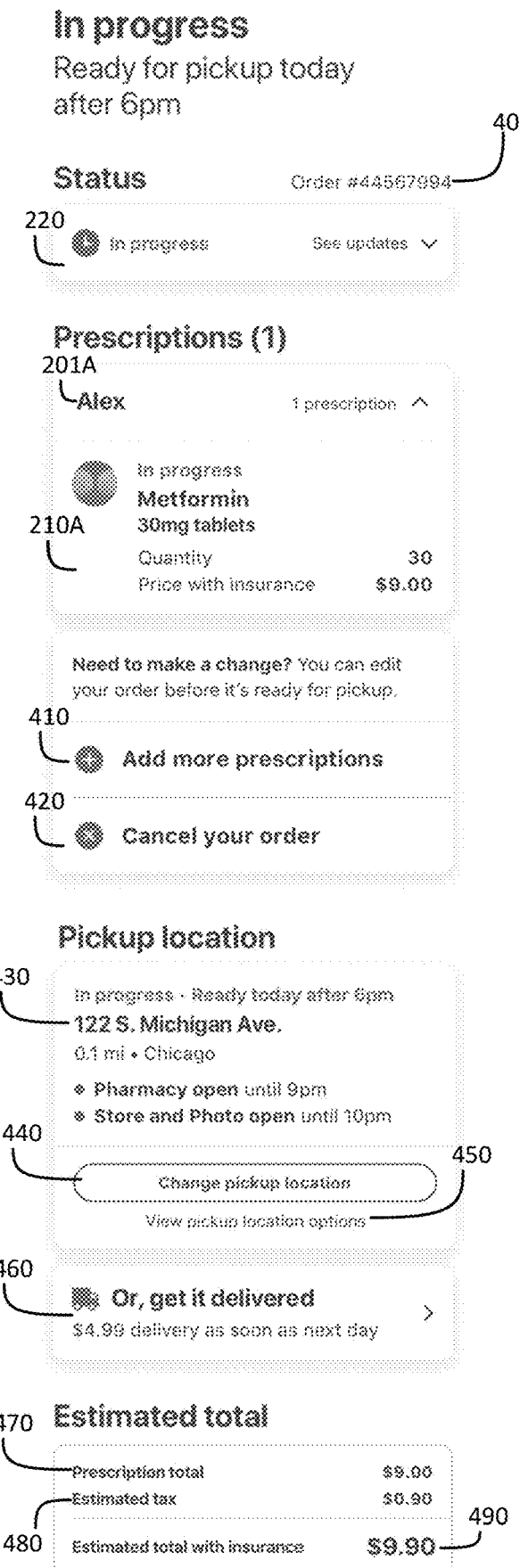
FIG. 4 shows a further example of a display displayed by an embodiment.

FIG. 4 shows a further example of a display displayed by app 112. In this regard, FIG. 4 illustrates an option for a user to add more prescriptions 410; an option for a user to cancel an order 420; a pickup location 430; an option to change pickup location 440; an option to view pickup locations 450, and order number 405. In addition, FIG. 4 illustrates features that are particularly specific to delivery of prescription medication. Specifically, FIG. 4 illustrates a prescription total 470, an estimated tax for the prescription 480, and an estimated total for the prescription including health insurance 490. Because some jurisdictions do not charge tax for prescription medication, the app 112 may determine that the relevant jurisdiction does not charge tax for prescription medication; and, in response to the determination, display the estimated tax as zero dollars.

Figure 5A:
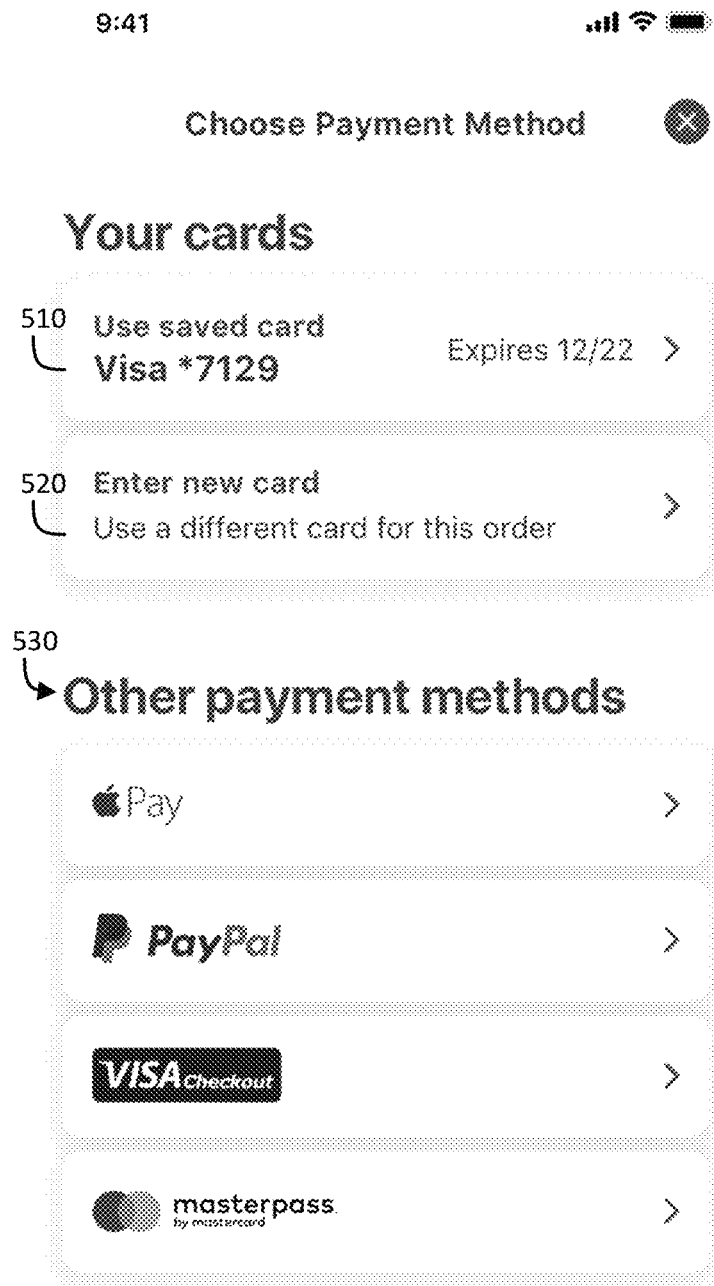
FIG. 5A illustrates an example payment screen.

FIG. 5A illustrates an example payment screen. With reference thereto, a user is given the option to use a saved credit card 510, an option to enter a new credit card 520, and an option to use another payment method 530.

Figure 5B:
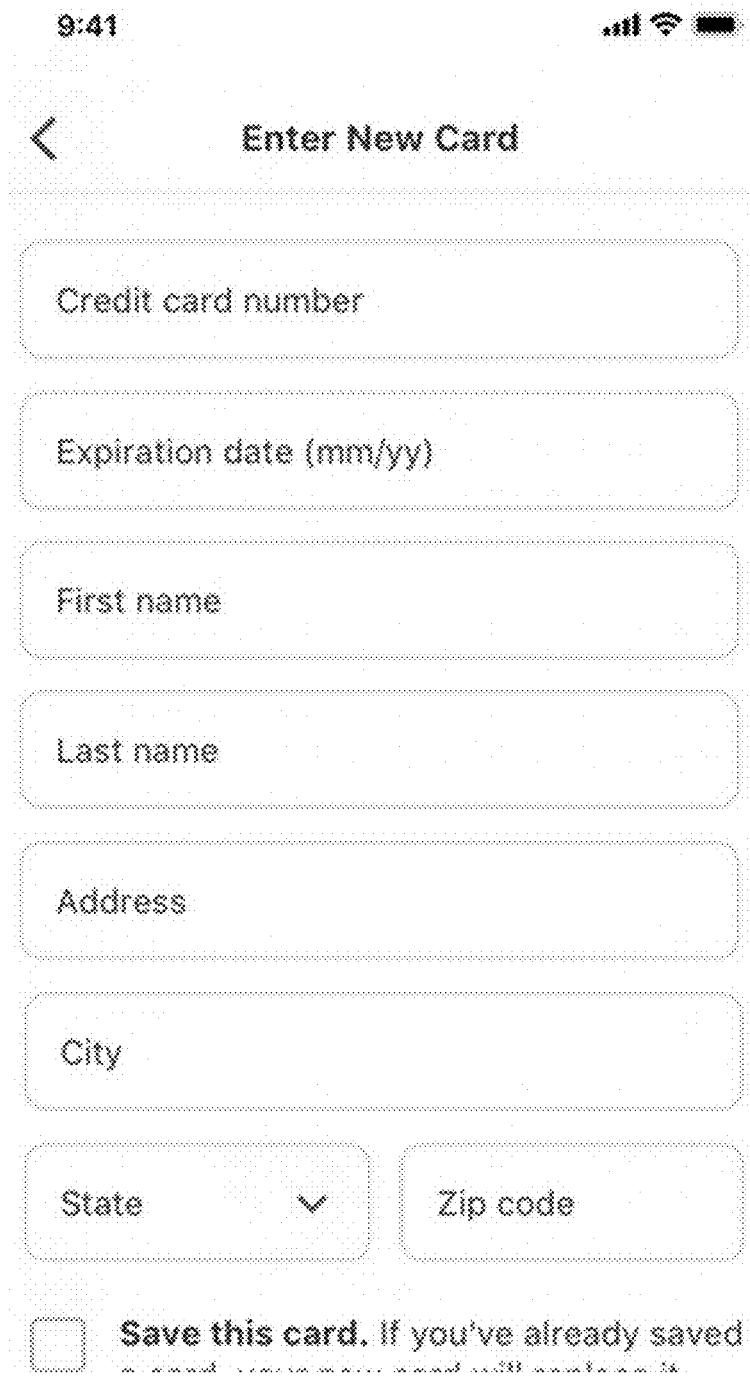
FIG. 5B illustrates an example of a screen for entry of credit card information.

FIG. 5B illustrates an example of a screen for entry of new credit card information.

Figure 5C:
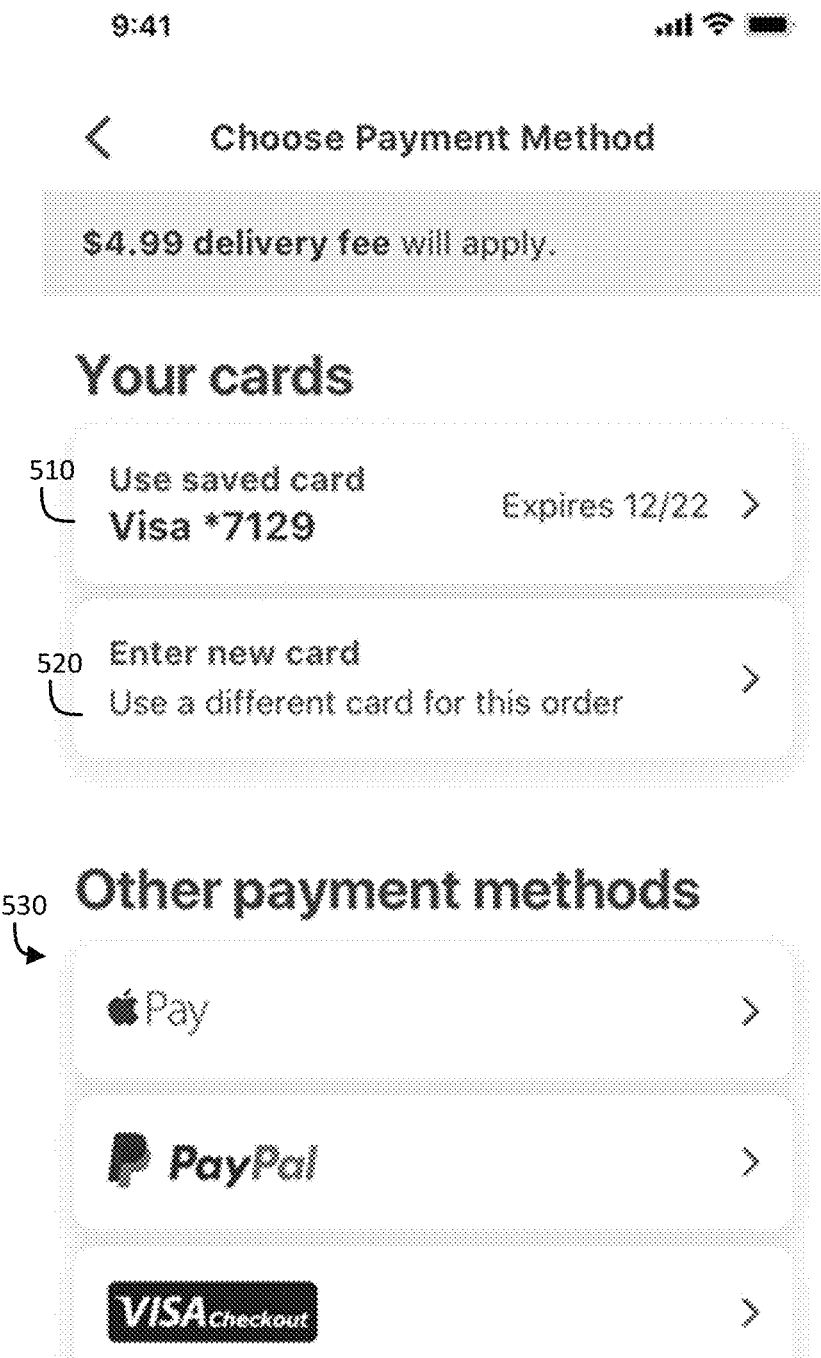
FIG. 5C illustrates an example of a payment screen where the user has selected home delivery for the prescription medication.

FIG. 5C illustrates an example of a payment screen where the user has selected home delivery for the prescription medication.

Figure 6:
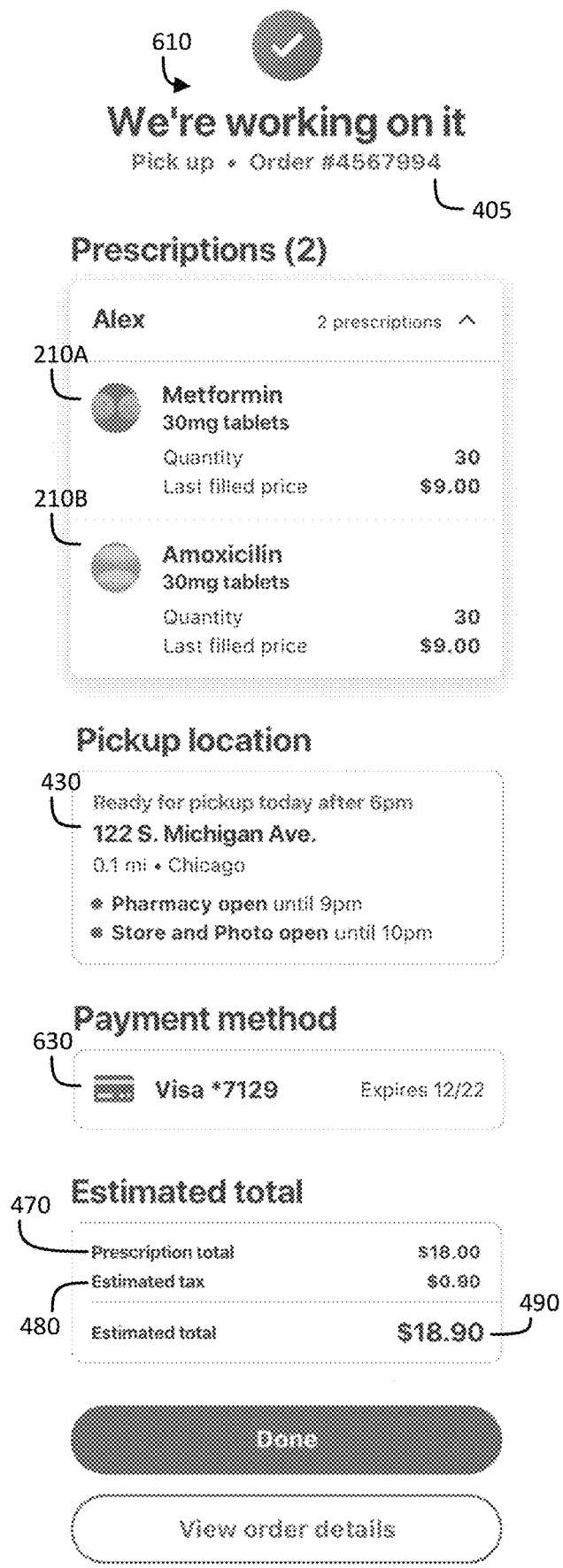
FIG. 6 illustrates an example confirmation screen that may be displayed after a user has confirmed a purchase.

FIG. 6 illustrates an example confirmation screen that may be displayed after a user has confirmed a purchase. In this regard, the example of FIG. 6 includes an indication that the order is being filled 610, and payment method 630.

FIG. 7 illustrates an example including fulfillment options 720. For example, a user is presented with a pickup in store option 730, and a deliver to user option 740. An option to remove a prescription 710 is further shown. In addition, prepay option 750 is offered to the user, which allows the user to prepay for the prescription medication so that time may be saved, for example, when the user picks up the prescription.

Figure 8:
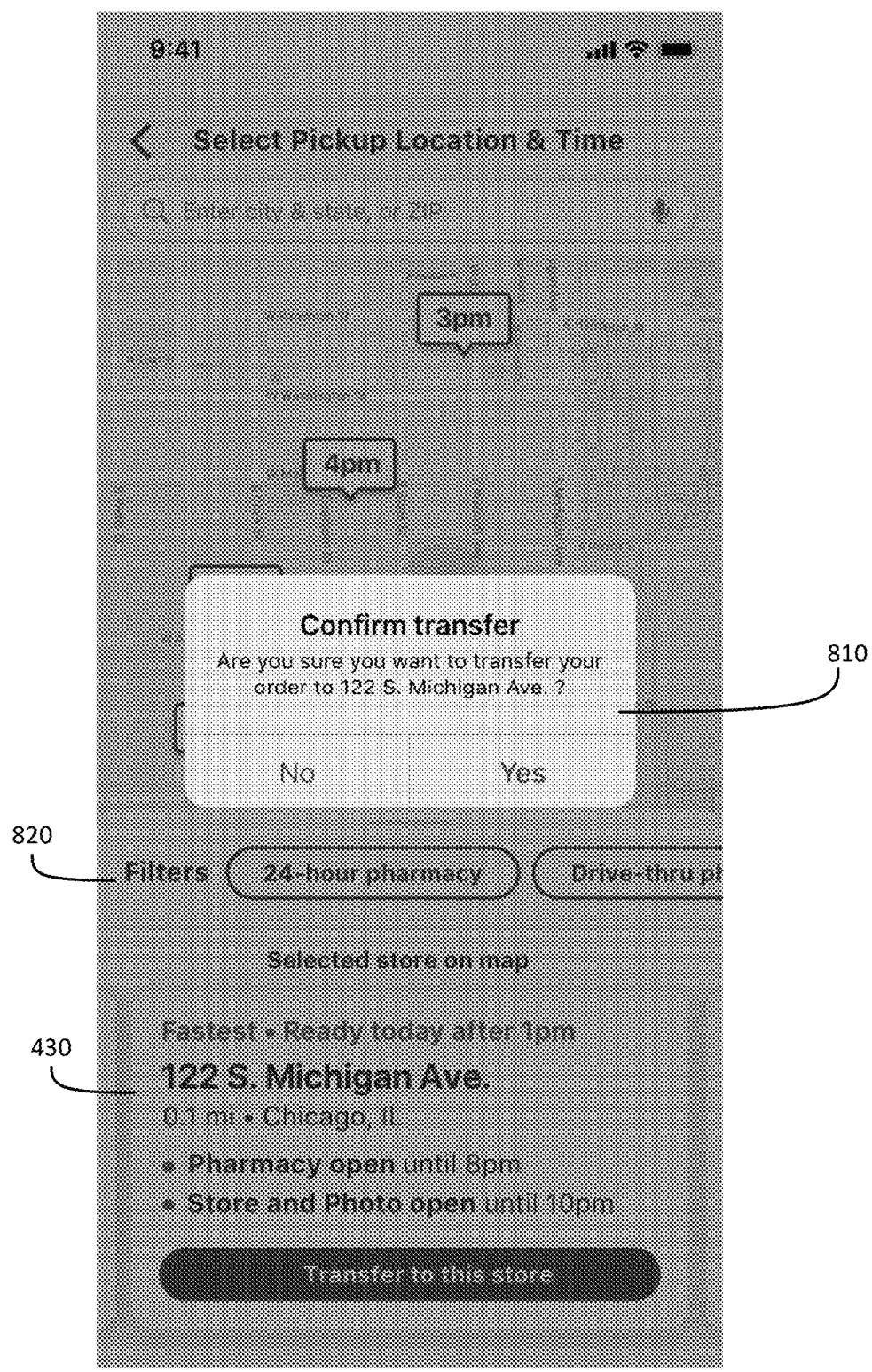
FIG. 8 illustrates an example confirmation screen of transferring a prescription from one pharmacy to another.

FIG. 8 illustrates an example confirmation screen of transferring a prescription from one pharmacy to another. In this regard, the confirm transfer box 810 allows a user to transfer a prescription from one pharmacy to another. For example, one or both of the first prescription 210A or second prescription 210B may be transferred between pharmacies. In addition, to aid the user in selecting a pharmacy, filters 820 may be applied (e.g., 24-hour pharmacy, drive-through pharmacy, option for locker pickup, option for curbside pickup, and so forth).

Figure 9A:
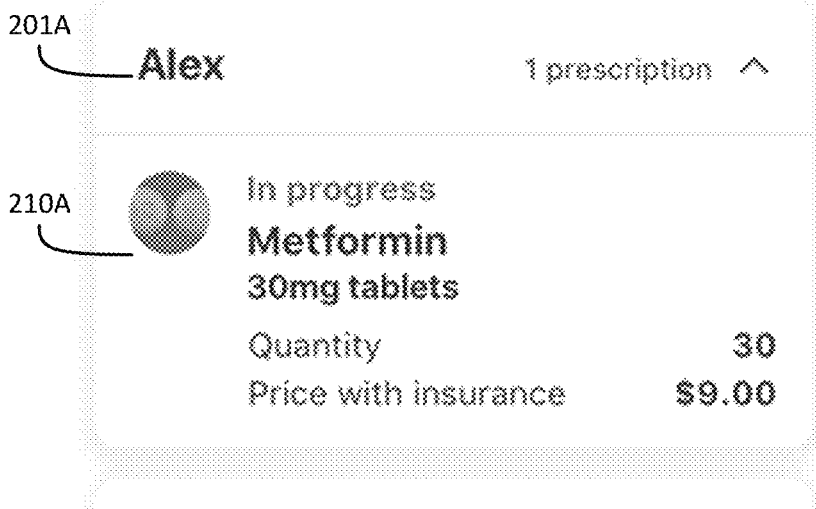
FIG. 9A illustrates an example of a screen indicating when a prescription medication will be ready for pickup after a certain time.

FIG. 9A illustrates an example of a screen indicating when a prescription medication will be ready for pickup after a certain time. The indication of when the prescription medication will be ready for pickup is made at progress indication 910. It should be noted that progress indication 910 may display a specific day, or a range of days. Additionally, the progress indication 910 may display a specific time or a range of times.

Figure 9B:
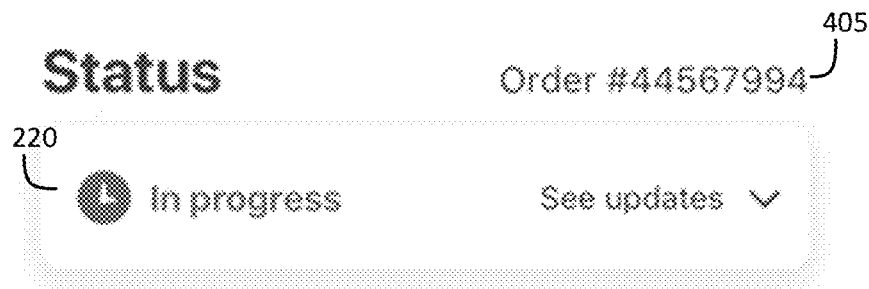
FIG. 9B illustrates an example of a screen indicating when a medication will arrive.

FIG. 9B illustrates an example of a screen indicating when a medication will arrive (e.g., to the user's home). The indication of when the prescription medication will arrive is made at progress indication 910. It should be noted that progress indication 910 may display a specific day, or a range of days. Additionally, the progress indication 910 may display a specific time or a range of times.

FIG. 10 illustrates an example of a screen for selecting an option for using a saved address 1010, or an option for using a new address 1020 for home delivery of the prescription medication.

Figure 11:
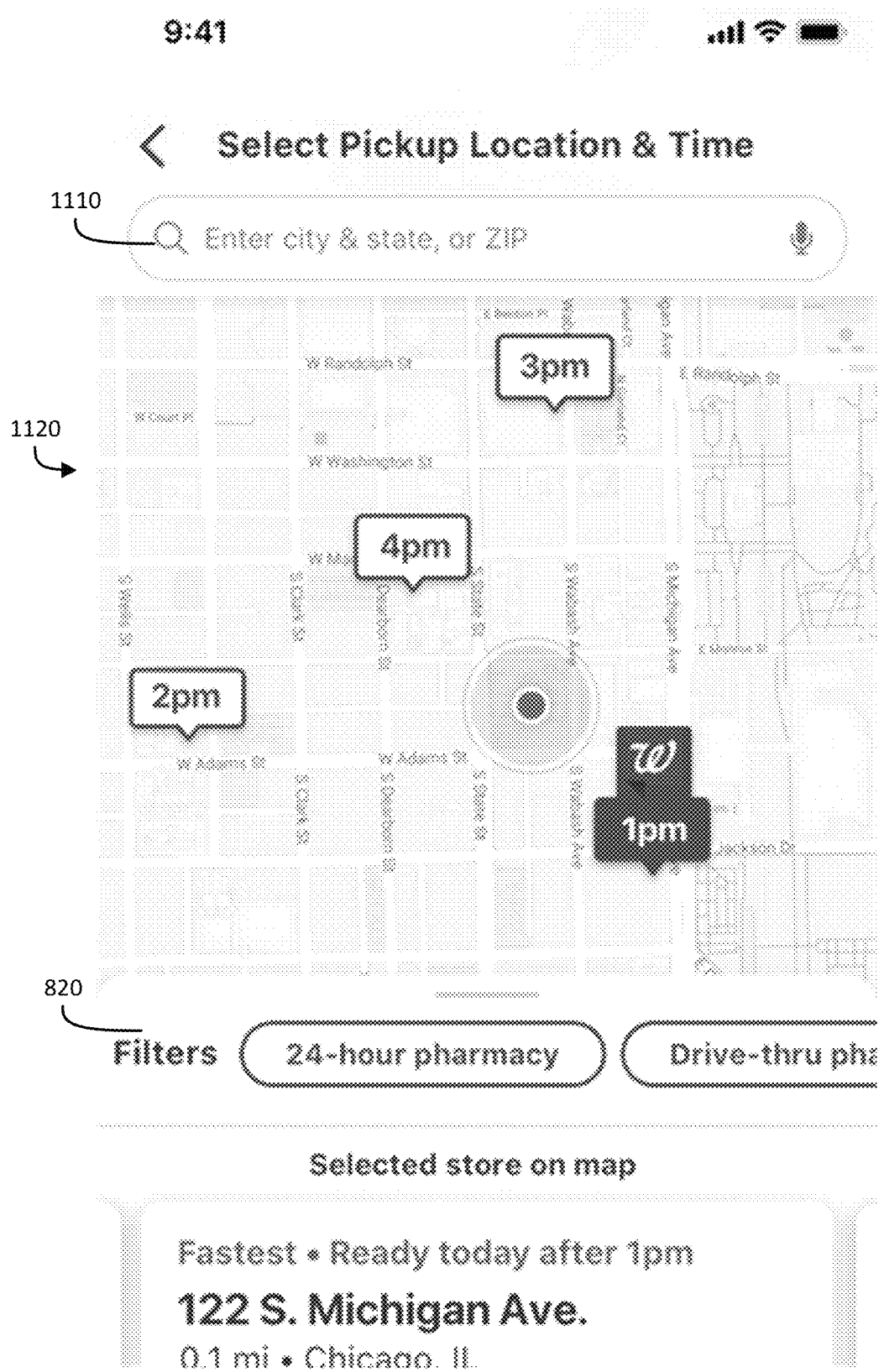
FIG. 11 illustrates an example of a screen displaying prescription medication pickup times on a map.

FIG. 11 illustrates an example of a screen displaying prescription medication pickup times on a map 1120. With reference thereto, a user may enter location information (e.g., address, zip code, or so forth) into search bar 1110, and the system will search for pharmacies near the entered location. The system will further calculate fill times for prescriptions of the order for each pharmacy near the entered location; and, based on the fill times, calculate an order pickup time (e.g., by selecting the latest fill time for a perception from each prescription within the order) for each pharmacy near the entered location. The app 112 may then display the order pickup times for each pharmacy on the map 1120.

Exemplary Processes

The following will discuss example processes of the systems and methods described herein. The blocks of the examples may be performed by any of the entities or combination of entities shown in FIG. 1. For instance, some or all of the blocks may be performed by app 112; or some or all of the blocks may be performed by the prescription order and delivery system 101. In some implementations, some of the blocks are performed by the app 112, while others are performed by the prescription order and delivery system 101.

Furthermore, some of the following examples reference first and second patients, medications, prescriptions, or pharmacies. However, it should be understood that the following principles may be applied equally to any number of patients, medications, prescriptions, or pharmacies (e.g., apply to a single patient, medication, prescription, or pharmacy; or to many patients, medications, prescriptions, or pharmacies). Moreover, it should be understood that many the blocks of the following examples may be performed in any order, and are not necessarily constrained by the order shown in the examples.

Figure 12:
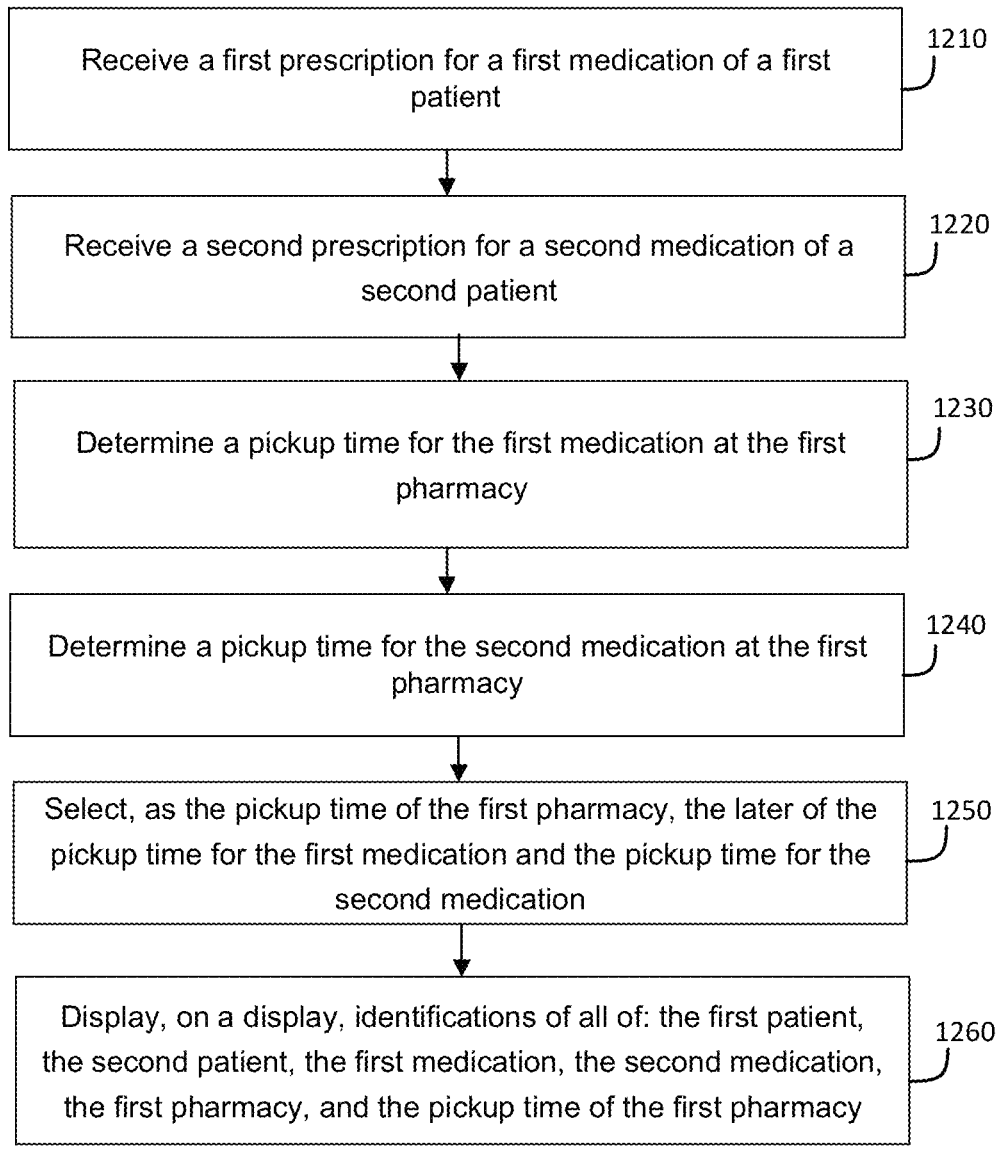
FIG. 12 shows an overview of an example method for calculating a pickup time of an order at a first pharmacy, and displaying order information.

FIG. 12 shows an overview of an example method for calculating a pickup time of an order at a first pharmacy, and displaying order information. At block 1210, a first prescription for a first medication for a first patient is received. At block 1220, a second prescription for a second medication of a second patient is received. At block 1230, a pickup time for the first medication at the first pharmacy is determined. At block 1240, a pickup time for the second medication at the first pharmacy is determined. In some embodiments, as part of determining the pickup times of the first and second medications, the system periodically (e.g., every hour) checks a warehouse (e.g., warehouse 160) inventory of medications. In some implementations, this checking is performed at the bottle level, and not the pill level. Furthermore, this checking may be used to indicate to a patient that a medication is out of stock (OOS).

At block 1250, as the pickup time of the first pharmacy, the later of the pickup time for the first medication and the pickup time for the second medication is selected. At block 1260, identifications of all of: the first patient, the second patient, the first medication, the second medication, the first pharmacy, and the pickup time of the first pharmacy are displayed on a display. In some embodiments, the first patient and the second patient are part of the same family. In this manner, app 112 may conveniently display information for all family members. The app may further display: (i) insurance information of any or all of the prescriptions or medications, and/or (ii) copayment information of any or all of the prescriptions or medications.

In some embodiments, a new prescription may be advantageously bundled (e.g., for delivery or pickup) together with a refill prescription. This may advantageously reduce the amount of trips to pharmacies that the patient must make, and further may save the pharmacy shipping costs. In some implementations of these embodiments, at block 1260, refill information may be further be displayed. Furthermore, the refill may be automatic, or may require confirmation from the user that the prescription is to be refilled.

In some embodiments, the system determines that a prescription may only be partially filled at a pharmacy (e.g., the pharmacy has only half the pills necessary to fill the prescription). If this determination is made, the user may be given the option of partially filling the prescription at the pharmacy, and filling the remaining portion of the prescription at a later time at the same or different pharmacy. In some embodiments, an indication on a map 1120 of the pickup time of the partially available prescription, as well as an indication that the prescription will only be partially available, may be displayed. In this regard, two times may be displayed: one time when the initial, partial prescription is available; and another time when the full prescription will be available.

Figure 13:
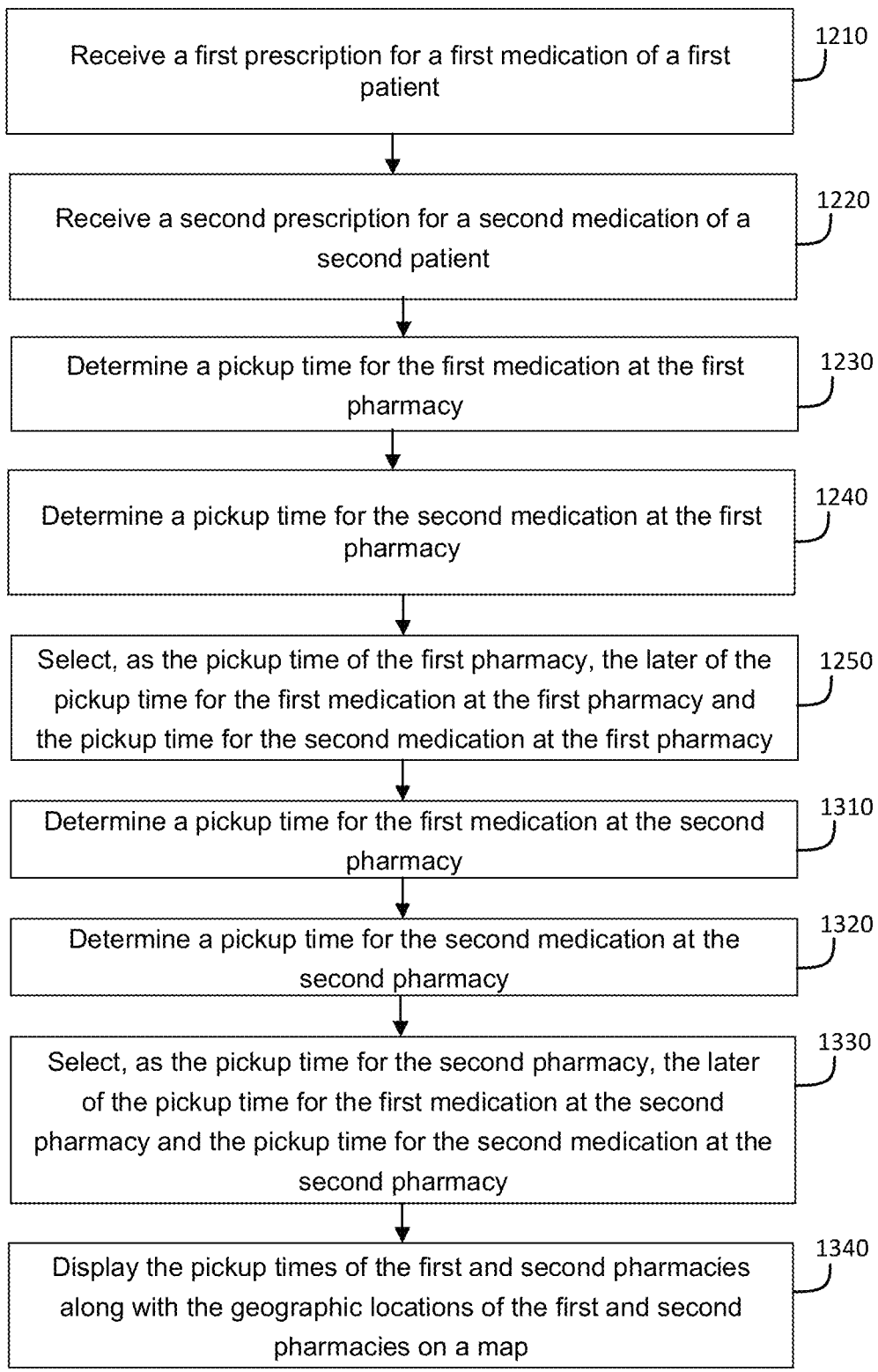
FIG. 13 shows an example method for calculating a pickup time of an order at two pharmacies, and displaying information on a map.

FIG. 13 shows an example method for calculating a pickup time of an order at two pharmacies, and displaying information on a map. In the example of FIG. 13, blocks 1210, 1220, 1230, 1240, 1250 are substantially similar to the corresponding blocks in the example of FIG. 12. At block 1310, a pickup time for the first medication at the second pharmacy is determined. At block 1320, a pickup time for the second medication at the second pharmacy is determined. At block 1330, the later of the pickup time for the first medication at the second pharmacy and the pickup time for the second medication at the second pharmacy is selected as the pickup time of the second pharmacy. At block 1340, the pickup times of the first and second pharmacies along with the geographic locations of the first and second pharmacies are displayed on a map.

Figure 14:
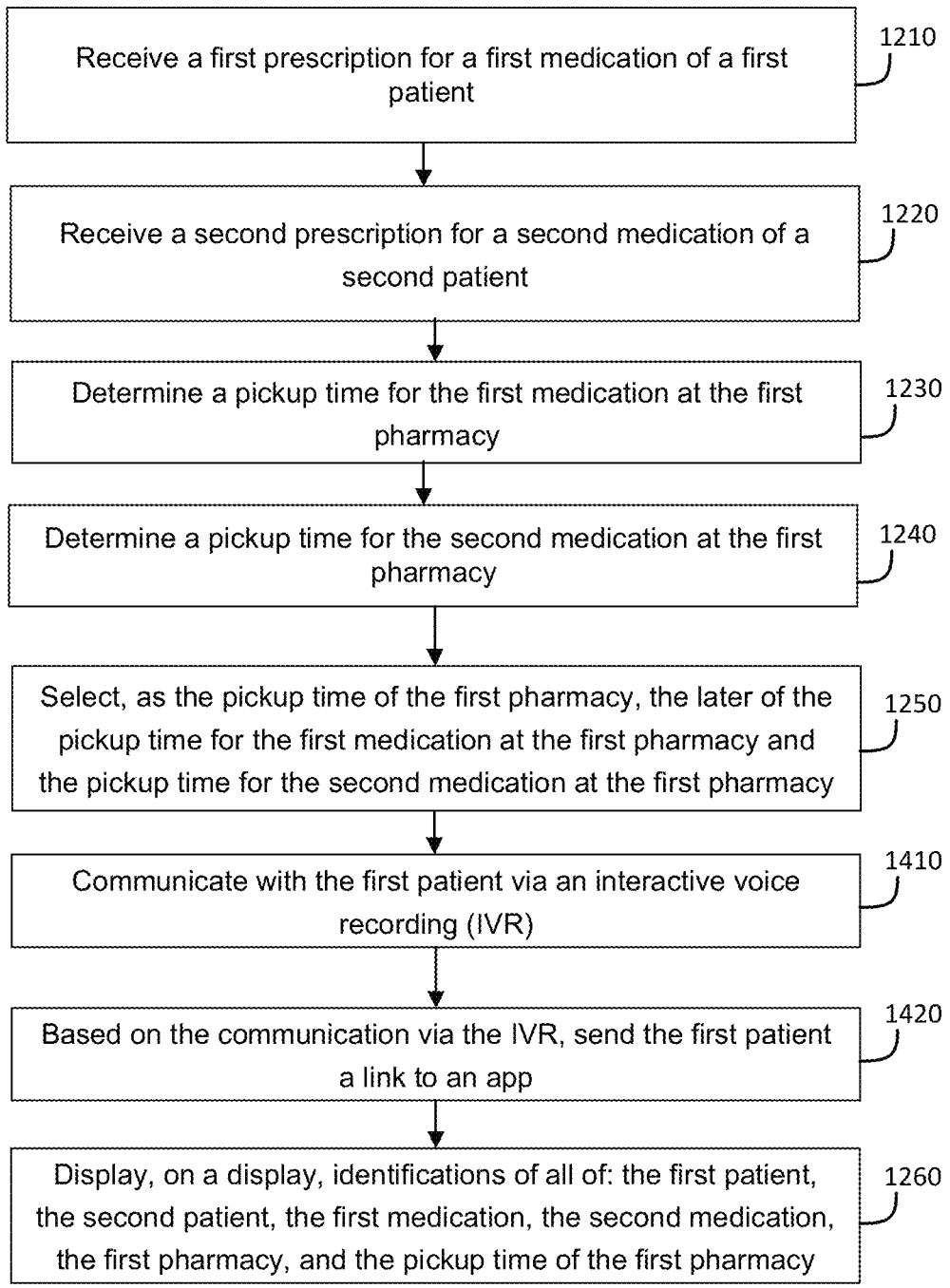
FIG. 14 shows an example relating to using an interactive voice recording (IVR).

FIG. 14 shows an example relating to using an interactive voice recording (IVR). In the example of FIG. 14, blocks 1210, 1220, 1230, 1240, 1250 are substantially similar to the corresponding blocks in the example of FIG. 12. At block 1410, the first patient may communicate (e.g., with the prescription order and delivery system 101) via an IVR. For example, the first patient may call a phone number of a pharmacy, and be connected to the IVR. At block 1420, based on the communication between the first patient and the IVR, the first patient may be sent a link (e.g., via text message or email). For instance, the user may request, via the IVR, that a link be sent to her. The link may link to an application such as app 112. In this way, pharmacies may encourage consumers to use the app 112 rather than communicate over the phone or in person at a store. Further, this technique "introduces" consumers to the app who might otherwise not be inclined to use an app. Block 1260 of FIG. 14 may be substantially similar to the corresponding block in FIG. 12. It should be understood that the display may be displayed by an app such as app 112, and that the app further allows a user to view and make changes to an order.

Figure 15:
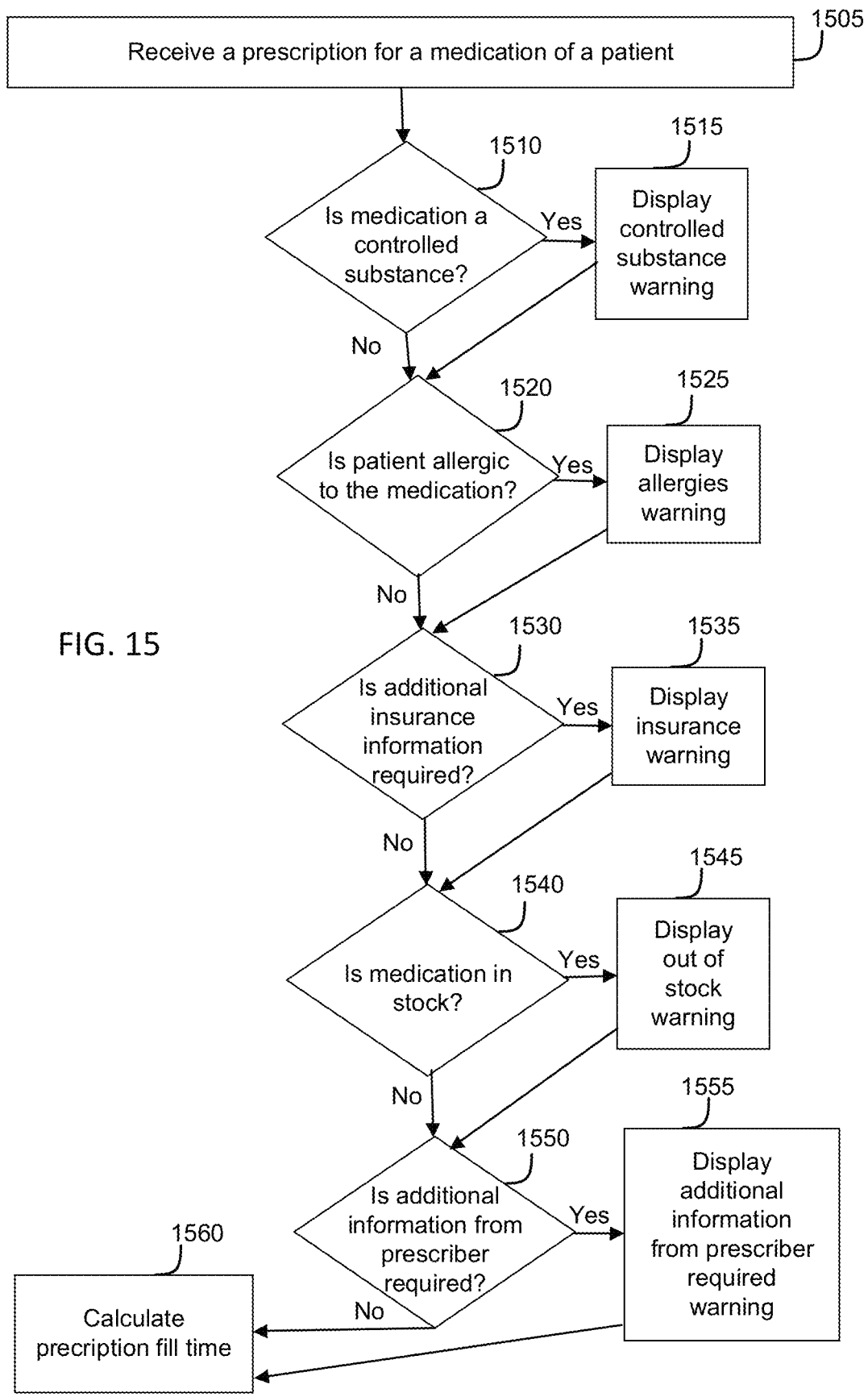
FIG. 15 illustrates an example including additional aspects such as additional checks of the prescription.

FIG. 15 illustrates an example including additional aspects such as additional checks of the prescription. At block 1505, a prescription for a medication for a patient is received. At block 1510, it is checked if the medication comprises a controlled substance. If so, at block 1515, a controlled substance warning is displayed. In some implementations, the controlled substance warning may indicate the medication must be picked up at a pharmacy that the patient has previously picked up the medication at.

In the example of FIG. 15, the method proceeds to block 1520 if the answer to the question in block 1510 is no, or after the warning is displayed in block 1515. At block 1520, it is checked if the patient is allergic to the medication. If so, at block 1525, an allergies warning is displayed. In some implementations, the allergies warning may indicate the allergies, suggest alternate medication, and/or include an indication that the medication is being delayed in filling.

The method proceeds to block 1530 if the answer to the question in block 1520 is no, or after the warning is displayed in block 1525. At block 1530, it is checked if additional insurance information is required. If so, at block 1535, an insurance warning is displayed. In some implementations, the insurance warning includes an indication that additional insurance information is required, and include an indication that the medication is being delayed in filling.

The method proceeds to block 1540 if the answer to the question in block 1530 is no, or after the warning is displayed in block 1535. At block 1540, it is checked if the medication is in stock. If so, at block 1545, an out of stock (OOS) warning is displayed. In some implementations, the OOS warning includes an indication that the medication is being delayed in filling. In some implementations, an OOS flag may be set to indicate that the medication is out of stock. For instance, in data sent from the prescription order and delivery system 101 to the app 112, an OOS flag may be set to indicate that the medication is out of stock at a warehouse.

The method proceeds to block 1550 if the answer to the question in block 1540 is no, or after the warning is displayed in block 1545. At block 1550, it is checked if additional information is required from the prescriber (e.g., healthcare provider 145). If so, at block 1555, an additional information from prescriber warning is displayed. In some implementations, the additional information from prescriber warning includes an indication that an additional information from prescriber is required, and includes an indication that the medication is being delayed in filling. At block 1560, prescription fill time is calculated. In some embodiments, this is done as in the examples of FIGS. 12-14.

In some embodiments, the system also checks whether the prescription may be filled at a pharmacy due to insurance reasons. If the prescription may not be filled at a pharmacy due to insurance reasons, a message is displayed indicating that the prescription may not be filled at a pharmacy due to insurance reasons.

In some embodiments, the system also checks if insurance information needs to be updated. If so, a request may be sent to the user for updated insurance information. In this regard, the user may update her insurance information through the app 112. For example, the user may take a photo of her insurance card and upload it through the app 112.

Figure 16:
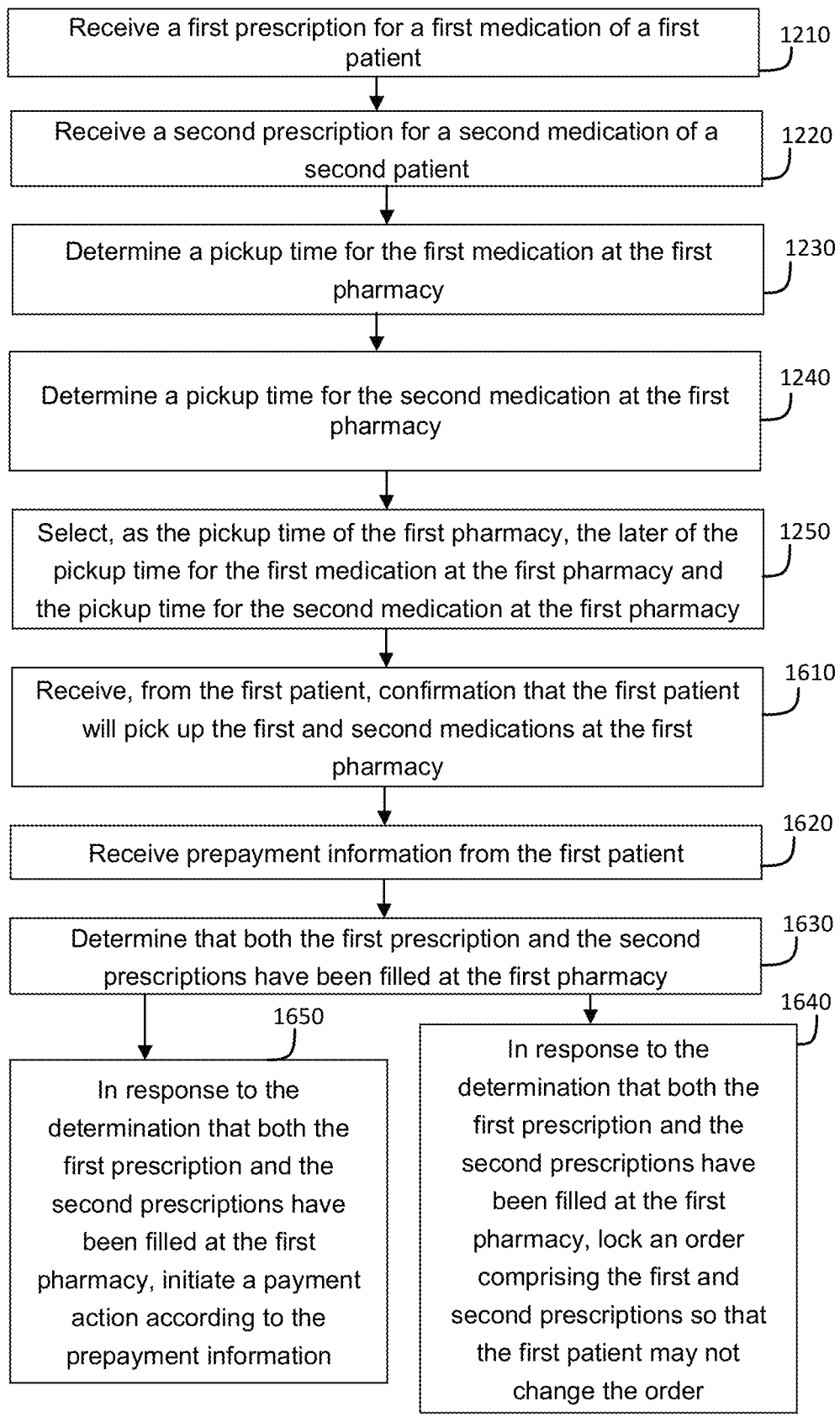
FIG. 16 shows an example method relating to actions taken when it is determined that the prescriptions have been filled.

FIG. 16 shows an example method relating to actions taken when it is determined that the prescriptions have been filled. In the example of FIG. 16, blocks 1210, 1220, 1230, 1240, 1250 are substantially similar to the corresponding blocks in the example of FIG. 12. At block 1610, the first patient confirms (e.g., through app 112, through an IVR technique, or through text message, etc.) that she will pick up the first and second medications at the first pharmacy. At block 1620, prepayment information is received from the first patient. In some implementations, at this point, a hold may be placed on an amount of money of a credit card of the first patient.

At block 1630, it is determined that both the first and second prescriptions have been filled at the first pharmacy. In some implementations, this determination is made by receiving confirmation from the first pharmacy that the prescriptions have been filled. In some embodiments, in response to the determination of block 1630, one or both of two actions are taken. First, a lock may be placed on the order comprising the first and second medications so that the first patient may not change the order (e.g., block 1640). Second, a payment action may be initiated according to the prepayment action (e.g., block 1650). In some embodiments, the payment action comprises releasing a hold on the amount of money on the credit card placed at block 1620. In some embodiments, the payment action comprises charging a credit card or transferring money from an account of the first patient.

Figure 17:
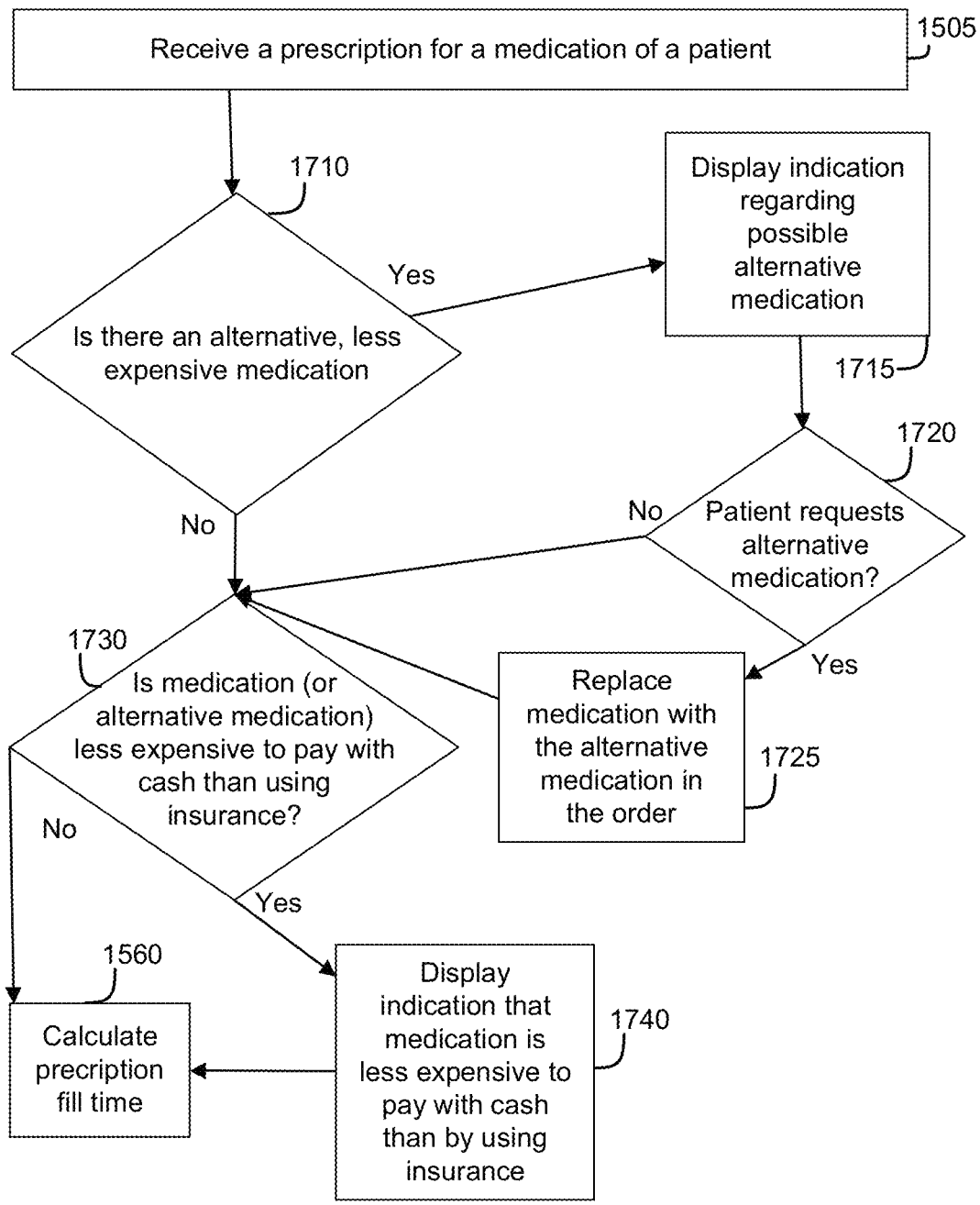
FIG. 17 shows an example method of reducing prescription costs for a user.

FIG. 17 shows an example method of reducing prescription costs for a user. At block 1505, a prescription for a medication for a patient is received. At block 1710, it is checked if there is an alternative, less expensive medication. If so, an indication regarding the possible alternative medication is displayed at block 1715. In response to the suggested possible alternative medication, the user may, at block 1720, request the alternative medication. If the user does request the alternative medication, the system replaces the medication in the order with the alternative medication at block 1725, and the example method proceeds to block 1730.

At block 1730, which also may be reached if the answer to blocks 1710 or 1720 is negative, the system checks if it is less expensive to pay for the medication (or alternative medication) with cash rather than by using insurance. If so, at block 1740, an indication is displayed indicating that it is less expensive to pay for the medication with cash rather than by using insurance. At block 1560, which may be reached after block 1740 or if the answer to block 1730 is negative, a prescription fill time is calculated.

Figure 18:
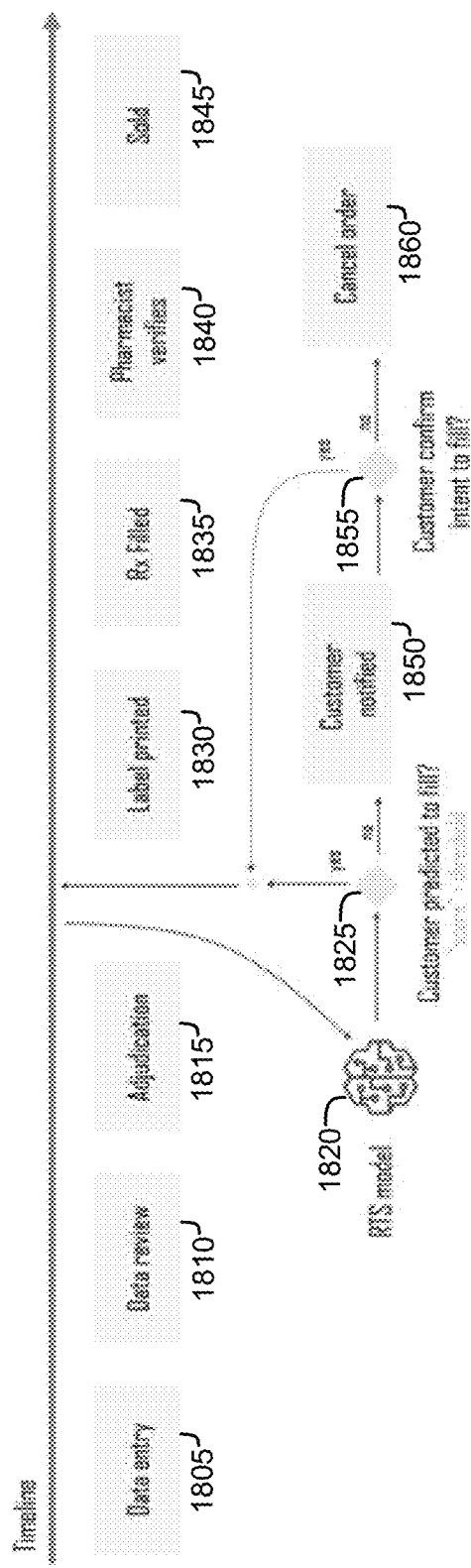
FIG. 18 illustrates an example method relating to whether a customer is predicted to fill a prescription.

In some implementations, it is useful to predict if a patient will pick up a prescription. This is advantageous because a pharmacy may then save resources by not filling a prescription that is not likely to be picked up. In this regard, in some embodiments, if it is predicted that a patient will not pick up a prescription, the pharmacy fills the prescription only after receiving confirmation from the patient that she will indeed pick up the medication. FIG. 18 shows such an example.

At block 1805, data (e.g., from a received prescription) is entered. At block 1810, the data is reviewed (e.g., for insurance information, allergies, conflicts between drugs, discounts, and so forth). At block 1815, the data is adjudicated (e.g., an initial determination is made as to whether the prescription will be filled). At block 1820, an AI model of the patient is created to determine if the patient is predicted to fill the prescription. The model may be based on past data collected about the patient (e.g., whether the patient has filled past prescriptions; what types of medications the patient typically purchases; if the present medication has previously purchased or filled by the patient; etc.). At block 1825, it is determined if the patient is predicted to fill the prescription. If so, at block 1830, a label is printed for the medication of the prescription. At block 1830, the prescription (Rx) is filled. At block 1840, the pharmacist verifies the prescription. At block 1845, the prescription is sold to the patient.

If the patient is predicted not to fill the prescription, the customer is sent a notification at block 1850. The notification may include a request for confirmation that the customer will purchase the prescription, and the request for confirmation may require the patient to respond during a predetermined time period. The notification may further include a request for payment or prepayment information. At block 1855 it is determined if the customer has confirmed that she intends to pick up the prescription. If so, the method returns to block 1830. If not, the order is cancelled at block 1860.

Additional Exemplary Embodiments

Aspect 1. A computer-implemented method for facilitating order and delivery of prescription medication, the method comprising:
  receiving a first prescription for a first medication of a first patient;
  receiving a second prescription for a second medication of a second patient;
  determining a pickup time of a first pharmacy by:
    determining a pickup time for the first medication at the first pharmacy;
    determining a pickup time for the second medication at the first pharmacy; and
    selecting, as the pickup time of the first pharmacy, the later of the pickup time for the first medication and the pickup time for the second medication; and
  displaying, on a display, identifications of all of: the first patient, the second patient, the first medication, the second medication, the first pharmacy, and the pickup time of the first pharmacy.

Aspect 2. The computer-implemented method of aspect 1, further comprising:
  receiving, from the first patient, confirmation that the first patient will pick up the first and second medications at the first pharmacy;
  receiving prepayment information from the first patient;
  determining that both the first prescription and the second prescriptions have been filled at the first pharmacy;
  in response to the determination that both the first prescription and the second prescriptions have been filled at the first pharmacy, initiating a payment action according to the prepayment information.

Aspect 3. The computer-implemented method of any of aspects 1-2, further comprising:
  determining a pickup time of a second pharmacy by:
    determining a pickup time for the first medication at the second pharmacy;
    determining a pickup time for the second medication at the second pharmacy; and
    selecting, as the pickup time of the second pharmacy, the later of the pickup time for the first medication at the second pharmacy and the pickup time for the second medication at the second pharmacy;
  displaying, on the display, an identification of the second pharmacy, and an identification of the pickup time of the second pharmacy; and
  receiving, from the first user, a selection of either the first pharmacy or the second pharmacy.

Aspect 4. The computer-implemented method of aspect 3, further comprising displaying, on the display, the identifications of the first pharmacy and the second pharmacy as geographic locations on a map.

Aspect 5. The computer-implemented method of any of aspects 1-4, further comprising:
communicating with the first patient via an interactive voice recording (IVR); and
based on the communication with the first patient, sending, to the first patient, a link, wherein: (i) the link is sent via text message or email, and (ii) the link links to an application (app) of the first pharmacy.

Aspect 6. The computer implemented method of any of aspects 1-5, wherein the app allows the first patent:
to view an order comprising all of: the first patient, the second patient, the first medication, the second medication, the first pharmacy, and the pickup time of the first pharmacy; and
make changes to the order.

Aspect 7. The computer-implemented method of any of aspects 1-6, further comprising:
determining that the first medication comprises a controlled substance; and
based on the determination that the first medication comprises a controlled substance, indicating to the first patient that the first patient will be allowed to pick up the first medication at a particular pharmacy only if the patient has previously picked up a type of medication corresponding to the first medication at the particular pharmacy.

Aspect 8. The computer-implemented method of any of aspects 1-7, further comprising:
building an artificial intelligence (AI) based model of the first patient;
based on the AI based model of the first patient, predicting that the first patient will not pick up the first medication; and
based on the prediction that the first patient will not pick up the first medication, requesting confirmation from the first patient that the first patient will fill the first prescription.

Aspect 9. The computer-implemented method of any of aspects 1-8, further comprising displaying, on the display: (i) insurance information of the first and second medications, and (ii) copayment information of the first and second medications.

Aspect 10. The computer-implemented method of any of aspects 1-9, further comprising:
checking insurance information of both the first prescription and the second prescription;
based on the checking, determining that additional insurance information is required; and
in response to the determination that additional information is required, displaying, on the display, an indication that an order comprising the first and second medication is delayed.

Aspect 11. The computer-implemented method of any of aspects 1-10, further comprising:
determining that the first patient has an allergy to the first medication; and
in response to the determination that the first patient has an allergy to the first medication, displaying, on the display, an indication that an order comprising the first medication is delayed.

Aspect 12. The computer-implemented method of any of aspects 1-11, further comprising:
determining that the first medication is out of stock; and
in response to the determination that the first medication is out of stock, displaying, on the display, an indication that an order comprising the first and second medications will be bifurcated.

Aspect 13. The computer-implemented method of any of aspects 1-12, further comprising:
determining that additional information is required from a prescriber before the first prescription may be filled; and
in response to the determination that additional information is required, displaying on the display, an indication that the first prescription must be reviewed with the prescriber.

Aspect 14. The computer-implemented method of any of aspects 1-13, further comprising:
receiving confirmation from either the first pharmacy or the second pharmacy that either the first or second prescription has been filled; and
in response to receiving the confirmation, locking an order comprising the first and second prescriptions so that the first patient may not change the order.

Aspect 15. The computer-implemented method of any of aspects 1-14, further comprising:
checking a warehouse for an inventory of the first medication, wherein the checking is performed at a bottle level, and is not performed at a pill level; and
based on the checking, displaying, on the display, an indication that the first medication is out of stock.

Aspect 16. The computer-implemented method of any of aspects 1-15, wherein:
the first medication is a new medication for the first patient; and
the method further comprises:
receiving a refill prescription for a refill medication of the first patient; and
bundling the new prescription with the refill prescription for delivery; and
the displaying further comprises displaying, on the display, an identification of the refill medication along with refill information of the refill medication.

Aspect 17. The computer-implemented method of any of aspects 1-16, further comprising:
determining that the first medication is less expensive to pay with cash than with an insurance contribution; and
in response to the determination that the first medication is less expensive to pay with cash than with the insurance contribution, displaying, on the display, an indication that the first medication is less expensive to pay with cash than with the insurance contribution.

Aspect 18. The computer-implemented method of any of aspects 1-17, further comprising:
receiving, from the first patient, a request for an alternative medication;
sending a message to a prescriber of the first medication requesting to replace the first medication with the alternative medication;
receiving, from the prescriber, a prescription for the alternative medication;
in response to receiving the prescription for the alternative medication, replacing the first medication with the alternative medication; and
displaying, on the display, an indication that the first medication has been replaced with the alternative medication.

Aspect 19. A computer system for facilitating order and delivery of prescription medication, the computer system comprising one or more processors configured to:

receive a first prescription for a first medication of a first patient;
receive a second prescription for a second medication of a second patient;
determine a pickup time of a first pharmacy by:
 determining a pickup time for the first medication at the first pharmacy;
 determining a pickup time for the second medication at the first pharmacy; and
 selecting, as the pickup time of the first pharmacy, the later of the pickup time for the first medication and the pickup time for the second medication; and
display, on a display, identifications of all of: the first patient, the second patient, the first medication, the second medication, the first pharmacy, and the pickup time of the first pharmacy.

Aspect 20. A computer system for facilitating order and delivery of prescription medication, comprising:
one or more processors; and
a program memory coupled to the one or more processors and storing executable instructions that when executed by the one or more processors cause the computer system to:
receive a first prescription for a first medication of a first patient;
receive a second prescription for a second medication of a second patient;
determine a pickup time of a first pharmacy by:
 determining a pickup time for the first medication at the first pharmacy;
 determining a pickup time for the second medication at the first pharmacy; and
 selecting, as the pickup time of the first pharmacy, the later of the pickup time for the first medication and the pickup time for the second medication; and
display, on a display, identifications of all of: the first patient, the second patient, the first medication, the second medication, the first pharmacy, and the pickup time of the first pharmacy.

Other Matters

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of geographic locations.

What is claimed:

1. A computer-implemented method for facilitating order and delivery of prescription medication, the method comprising:
 receiving, via one or more server processors, a first prescription for a first medication of a first patient;

receiving, via the one or more server processors, a second prescription for a second medication of a second patient;

determining, via the one or more server processors, a pickup time of a first pharmacy by:
  determining a pickup time for the first medication at the first pharmacy;
  determining a pickup time for the second medication at the first pharmacy; and
  selecting, as the pickup time of the first pharmacy, the later of the pickup time for the first medication and the pickup time for the second medication;

causing a display of a mobile device to display identifications of all of: the first patient, the second patient, the first medication, the second medication, the first pharmacy, and the pickup time of the first pharmacy;

determining, via the one or more server processors, a pickup time of a second pharmacy by:
  determining a pickup time for the first medication at the second pharmacy;
  determining a pickup time for the second medication at the second pharmacy; and
  selecting, as the pickup time of the second pharmacy, the later of the pickup time for the first medication at the second pharmacy and the pickup time for the second medication at the second pharmacy;

causing the display of the mobile device to display an identification of the second pharmacy, and an identification of the pickup time of the second pharmacy;

receiving, from the mobile device, a selection of either the first pharmacy or the second pharmacy; and instructing either the first pharmacy or the second pharmacy to fill the first prescription and the second prescription.

2. The computer-implemented method of claim 1, further comprising:
  receiving, from the first patient, confirmation that the first patient will pick up the first and second medications at the first pharmacy;
  receiving prepayment information from the first patient;
  determining that both the first prescription and the second prescription have been filled at the first pharmacy; and
  in response to the determination that both the first prescription and the second prescription have been filled at the first pharmacy, initiating a payment action according to the prepayment information.

3. The computer-implemented method of claim 1, further comprising causing the display of the mobile device to display the identifications of the first pharmacy and the second pharmacy as a geographic locations on a map.

4. The computer-implemented method of claim 1, further comprising:
  communicating with the first patient via an interactive voice recording (IVR); and
  based on the communication with the first patient, sending, to the first patient, a link, wherein: (i) the link is sent via text message or email, and (ii) the link links to an application (app) of the first pharmacy.

5. The computer-implemented method of claim 4, wherein the app allows the first patient to:
  view an order comprising all of: the first patient, the second patient, the first medication, the second medication, the first pharmacy, and the pickup time of the first pharmacy; and
  make changes to the order.

6. The computer-implemented method of claim 1, further comprising:
  determining that the first medication comprises a controlled substance; and
  based on the determination that the first medication comprises a controlled substance, indicating to the first patient that the first patient will be allowed to pick up the first medication at a particular pharmacy only if the first patient has previously picked up a type of medication corresponding to the first medication at the particular pharmacy.

7. The computer-implemented method of claim 1, further comprising:
  building an artificial intelligence (AI) based model of the first patient;
  based on the AI based model of the first patient, predicting that the first patient will not pick up the first medication; and
  based on the prediction that the first patient will not pick up the first medication, requesting confirmation from the first patient that the first patient will fill the first prescription.

8. The computer-implemented method of claim 1, further comprising causing the display to further display: (i) insurance information of the first and second medications, and (ii) copayment information of the first and second medications.

9. The computer-implemented method of claim 1, further comprising:
  checking insurance information of both the first prescription and the second prescription;
  based on the checking, determining that additional insurance information is required; and
  in response to the determination that additional information is required, causing the display to further display an indication that an order comprising the first and second medication is delayed.

10. The computer-implemented method of claim 1, further comprising:
  determining that the first patient has an allergy to the first medication; and
  in response to the determination that the first patient has an allergy to the first medication, causing the display to further display an indication that an order comprising the first medication is delayed.

11. The computer-implemented method of claim 1, further comprising:
  determining that the first medication is out of stock; and
  in response to the determination that the first medication is out of stock, causing the display to further display an indication that an order comprising the first and second medications will be bifurcated.

12. The computer-implemented method of claim 1, further comprising:
  determining that additional information is required from a prescriber before the first prescription may be filled; and
  in response to the determination that additional information is required, causing the display to further display an indication that the first prescription must be reviewed with the prescriber.

13. The computer-implemented method of claim 1, further comprising:
  receiving confirmation from either the first pharmacy or the second pharmacy that either the first or second prescription has been filled; and
  in response to receiving the confirmation, locking an order comprising the first and second prescriptions so that the first patient may not change the order.

14. The computer-implemented method of claim 1, further comprising:
   checking a warehouse for an inventory of the first medication, wherein the checking is performed at a bottle level, and is not performed at a pill level; and
   based on the checking, causing the display to further display an indication that the first medication is out of stock.

15. The computer-implemented method of claim 1, wherein:
   the first medication is a new medication for the first patient; and
   the method further comprises:
      receiving a refill prescription for a refill medication of the first patient; and
      bundling the new medication with the refill medication for delivery; and
   causing the display to further display an identification of the refill medication along with refill information of the refill medication.

16. The computer-implemented method of claim 1, further comprising:
   determining that the first medication is less expensive to pay with cash than with an insurance contribution; and
   in response to the determination that the first medication is less expensive to pay with cash than with the insurance contribution, causing the display to further display an indication that the first medication is less expensive to pay with cash than with the insurance contribution.

17. The computer-implemented method of claim 1, further comprising:
   receiving, from the first patient, a request for an alternative medication;
   sending a message to a prescriber of the first medication requesting to replace the first medication with the alternative medication;
   receiving, from the prescriber, a prescription for the alternative medication;
   in response to receiving the prescription for the alternative medication, replacing the first medication with the alternative medication; and
   causing the display to further display an indication that the first medication has been replaced with the alternative medication.

18. A computer system for facilitating order and delivery of prescription medication, the computer system comprising:
   one or more server processors configured to:
      receive a first prescription for a first medication of a first patient;
      receive a second prescription for a second medication of a second patient;
      determine a pickup time of a first pharmacy by:
         determining a pickup time for the first medication at the first pharmacy;
         determining a pickup time for the second medication at the first pharmacy; and
         selecting, as the pickup time of the first pharmacy, the later of the pickup time for the first medication and the pickup time for the second medication;
      cause a display of a mobile device to display identifications of all of: the first patient, the second patient, the first medication, the second medication, the first pharmacy, and the pickup time of the first pharmacy;
      determine a pickup time of a second pharmacy by:
         determining a pickup time for the first medication at the second pharmacy;
         determining a pickup time for the second medication at the second pharmacy; and
         selecting, as the pickup time of the second pharmacy, the later of the pickup time for the first medication at the second pharmacy and the pickup time for the second medication at the second pharmacy;
      cause the display of the mobile device to display an identification of the second pharmacy, and an identification of the pickup time of the second pharmacy;
      receive, from the mobile device, a selection of either the first pharmacy or the second pharmacy; and
      instruct either the first pharmacy or the second pharmacy to fill the first prescription and the second prescription.

19. A computer system for facilitating order and delivery of prescription medication, comprising:
   one or more server processors; and
   a program memory coupled to the one or more server processors and storing executable instructions that when executed by the one or more server processors cause the computer system to:
   receive a first prescription for a first medication of a first patient;
   receive a second prescription for a second medication of a second patient;
   determine a pickup time of a first pharmacy by:
      determining a pickup time for the first medication at the first pharmacy;
      determining a pickup time for the second medication at the first pharmacy; and
      selecting, as the pickup time of the first pharmacy, the later of the pickup time for the first medication and the pickup time for the second medication;
   cause a display of a mobile device to display identifications of all of: the first patient, the second patient, the first medication, the second medication, the first pharmacy, and the pickup time of the first pharmacy;
   determine a pickup time of a second pharmacy by:
      determining a pickup time for the first medication at the second pharmacy;
      determining a pickup time for the second medication at the second pharmacy; and
      selecting, as the pickup time of the second pharmacy, the later of the pickup time for the first medication at the second pharmacy and the pickup time for the second medication at the second pharmacy;
   cause the display of the mobile device to display an identification of the second pharmacy, and an identification of the pickup time of the second pharmacy;
   receive, from the mobile device, a selection of either the first pharmacy or the second pharmacy; and
   instruct either the first pharmacy or the second pharmacy to fill the first prescription and the second prescription.

* * * * *